United States Patent [19]
Pilato et al.

[11] Patent Number: 5,637,607
[45] Date of Patent: Jun. 10, 1997

[54] PESTICIDAL 1-ARYLPYRAZOLES

[75] Inventors: Michael T. Pilato, Cary; Tai-Teh Wu, Chapel Hill, both of N.C.

[73] Assignee: Rhone-Poulenc Inc., Research Triangle Park, N.C.

[21] Appl. No.: 688,952

[22] Filed: Jul. 31, 1996

Related U.S. Application Data

[63] Continuation-in-part of Ser. No. 588,840, Jan. 19, 1996, abandoned, which is a continuation of Ser. No. 426,657, Apr. 21, 1995, abandoned, which is a continuation-in-part of Ser. No. 390,028, Feb. 17, 1995, abandoned.

[30] Foreign Application Priority Data

Feb. 5, 1996 [ZA] South Africa ............... 960889
Feb. 8, 1996 [WO] WIPO ............ PCT/EP96/00527

[51] Int. Cl.⁶ ............... A01N 43/56; C07D 231/44
[52] U.S. Cl. ............... 514/404; 514/407; 548/367.4; 548/368.1; 548/368.4; 548/369.1
[58] Field of Search ............... 548/367.4, 369.1; 514/404, 407

[56] References Cited

U.S. PATENT DOCUMENTS

| | | | |
|---|---|---|---|
| 5,232,940 | 8/1993 | Hatton et al. | 514/407 |
| 5,451,598 | 9/1995 | Salmon | 514/404 |

FOREIGN PATENT DOCUMENTS

| | | |
|---|---|---|
| 0295117 | 12/1988 | European Pat. Off. . |
| 87/03781 | 7/1987 | WIPO . |
| 93/06089 | 4/1993 | WIPO . |
| 94/21606 | 9/1994 | WIPO . |

*Primary Examiner*—Robert W. Ramsuer
*Attorney, Agent, or Firm*—Burns, Doane, Swecker & Mathis, L.L.P.

[57] ABSTRACT

Compounds of the formula 1-(4-$SF_5$ 2-$R^2$ 6-$R^6$ phenyl) 3-CN 4-$S(O)_n R^4$ 5-$N(R^1)(R^3)$ pyrazole, pesticidal compositions comprising them and related methods of controlling pests are disclosed.

21 Claims, No Drawings

PESTICIDAL 1-ARYLPYRAZOLES

CROSS REFERENCE TO RELATED APPLICATIONS

This application is a continuation-in-part of U.S. application Ser. No. 08/588,840 filed Jan. 19, 1996 now abandoned, which is a File Wrapper Continuation of U.S. application Ser. No. 08/426,657 filed Apr. 21, 1995 now abandoned, which is a continuation-in-part of U.S. application Ser. No. 08/390,028, filed Feb. 17, 1995 now abandoned, all of which are incorporated herein by reference and relied upon.

BACKGROUND OF THE INVENTION

1. Field of the Invention

The invention relates to new 4-(sulfur containing substituent) derivatives of 1-arylpyrazoles, and derivatives thereof. The invention further pertains to compositions of said compounds and methods, using said compounds, for the control of arthropod, nematode, helminth or protozoan pests, in particular, to the application of said compounds or compositions in agricultural methods of use, particularly as pesticides, especially for controlling arthropods, most especially insects by systemic action.

2. Description of the Related Art

International Patent Publication No. WO 93/06089 (and the equivalent U.S. Pat. No. 5,451,598) and WO 94/21606 describe insecticidal 1-(4-$SF_5$ substituted phenyl) heterocycles which can be pyrroles as well as imidazoles or pyrazoles.

It is an object of the present invention to provide new pesticidal compounds of the 1-arylpyrazole family together with processes for their preparation.

A second object of the present invention is to provide pesticidal compositions and pesticidal methods of use of the pesticidal pyrazole compounds against arthropods, especially insects, plant nematodes, or helminth or protozoan pests, particularly in agricultural or horticultural crops, forestry, veterinary medicine or livestock husbandry, or in public health.

A third object of the present invention is to provide compounds with improved systemicity, that is, having improved systemic activity. A high systemicity enables the compounds to work well, even under dry conditions.

A fourth object of the present invention is to provide compounds with improved mammalian safety, that is to say, with less toxicity.

These and other objects of the invention shall become readily apparent from the description of the present invention which follows, and are achieved in whole or in part by the invention.

SUMMARY OF THE INVENTION

This invention provides improved insecticidal pyrazoles having the formula:

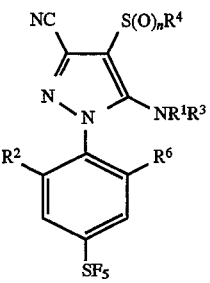

wherein:

each of $R^2$ and $R^6$, which are identical or different, is hydrogen, halogen, CN, alkyl, haloalkyl or alkylthio;

$R^4$ is lower alkyl;

n is 0, 1 or 2;

each of $R^1$ and $R^3$, which are identical or different, is H, lower alkyl, lower alkyl-$S(O)_n$, formyl, alkenyl, alkynyl, alkoxycarbonyl, alkylthiocarbonyl, aroyl or alkylcarbonyl, the alkyl portion of which radicals is optionally substituted by one or more $R^5$; or $R^1$ and $R^3$ are joined so as together to form a divalent radical having 4 to 6 atoms in the chain, this divalent radical being alkylene, alkyleneoxyalkylene or alkyleneaminoalkylene;

$R^5$ is cyano, nitro, alkoxy, haloalkoxy, $R^7S(O)_n$, alkoxycarbonyl, alkylcarbonyl, aminocarbonyl, alkylaminocarbonyl, dialkylaminocarbonyl, hydroxycarbonyl, halogen, hydroxy, aminosulfonyl, alkylaminosulfonyl or dialkylaminosulfonyl; and $R^7$ is lower alkyl or lower haloalkyl.

These compounds possess excellent properties in controlling important pests, such as aphids and whitefly in foliar applications and cotton leaf aphid (*Aphis gossypii*) and greenbug (*Schizaphis graminum*) in systemic applications.

DETAILED DESCRIPTION OF THE INVENTION

In the instant invention, some words are used in a specific sense: The term "aminocarbonyl" means a carbamoyl radical, that is, a radical of the formula —C(=O)$NH_2$. Similarly, the term "alkylaminocarbonyl" means an alkylcarbamoyl radical, that is, a radical of the formula —C(=O)NH-alkyl; and the term "dialkylaminocarbonyl" means a dialkylcarbamoyl radical, that is, a radical of the formula —C(=O)N(alkyl)$_2$ in which the alkyl moieties can be the same or different.

The term "hydroxycarbonyl" means a carboxyl radical, that is, —COOH. The term "aminosulfonyl" means a sulfamoyl radical, that is, —$SO_2NH_2$. Similarly, the term "alkylaminosulfonyl" means an alkylsulfamoyl radical, that is, a radical of the formula —$SO_2$NH-alkyl; while the term "dialkylaminosulfonyl" means a dialkylsulfamoyl radical, which has the formula —$SO_2$N(alkyl)$_2$ wherein the alkyl moieties can be the same or different.

The term "alkylcarbonyl" means an alkanoyl radical, that is, a radical of the formula —C(=O)-alkyl.

The term "halo" before the name of a radical means that this radical is partially or completely halogenated, that is to say, substituted by F, Cl, Br or I, in any combination, preferably by F or Cl. The term "halogen" means F, Cl, Br or I.

The term "aroyl" designates an arylcarbonyl radical, i.e., a radical of the formula —C(=O)-aryl, in which "aryl" is an aromatic radical, preferably phenyl, optionally substituted with one or more substituents such as halogen, methyl and methoxy; most preferably, the aroyl radical is a benzoyl, methylbenzoyl, halobenzoyl or xylylcarbonyl radical.

The various individual aliphatic hydrocarbon moieties, that is, radicals and portions thereof having a non-cyclic, non-aromatic hydrocarbon skeleton (such as, for example, alkenyl, alkynyl, the alkyl portions of alkoxycarbonyl and alkylthiocarbonyl, etc.) generally have up to 7 carbon atoms. Use of the term "lower" before the name of such an aliphatic hydrocarbon moiety means that the moiety has up to 4 carbon atoms; for example, "lower alkyl" means $C_1$–$C_4$ alkyl. Unless otherwise specified, the various aliphatic hydrocarbon moieties are preferably lower radicals.

When the name of a substituent is repeated, it retains the same meaning unless otherwise specified.

When $R^1$ and $R^3$ are joined together to form a divalent radical, it is preferred that —$NR^1R^3$ together form a morpholino, pyrrolidinyl, piperidino or piperazinyl radical.

Particularly preferred compounds of formula (I) above are those wherein $R^4$ is methyl, ethyl or propyl, and/or wherein $R^1$ is hydrogen and $R^3$ is hydrogen or alkyl, and/or wherein each of $R^2$ and $R^6$, which are identical or different, is H, Cl, Br or F.

Compounds of formula (I) in which n is zero or one are also preferred.

A preferred class of compound of formula (I) are those wherein:

$R^1$ and $R^3$ each represent hydrogen;

$R^2$ and $R^6$ each represent chlorine;

$R^4$ represents methyl or ethyl;

and n is zero, 1 or 2.

The following representative compounds of formula (I) form part of the present invention. In the Table below Et represents ethyl ($CH_2CH_3$).

| Cpd. No. | $R^1$ | $R^2$ | $R^6$ | $R^3$ | $R^4$ | n |
|---|---|---|---|---|---|---|
| 1 | H | Cl | Cl | H | $CH_3$ | 0 |
| 2 | H | Cl | Cl | H | $CH_3$ | 1 |
| 3 | H | Cl | Cl | H | Et | 0 |
| 4 | H | Cl | Cl | H | Et | 1 |
| 5 | H | Cl | Cl | H | Et | 2 |
| 6 | H | Cl | Cl | H | $CH_3$ | 2 |
| 7 | H | Cl | Br | H | $CH_3$ | 0 |
| 8 | H | Cl | Br | H | $CH_3$ | 1 |
| 9 | $CH_3$ | Cl | Cl | H | $CH_3$ | 1 |
| 10 | $CH_3$ | Cl | Cl | H | Et | 1 |
| 11 | Et | Cl | Cl | H | Et | 1 |
| 12 | Et | Cl | Cl | H | $CH_3$ | 1 |
| 13 | $CH_2CH_2CN$ | Cl | Cl | H | Et | 1 |
| 14 | $CH_2CH_2CN$ | Cl | Cl | H | $CH_3$ | 1 |
| 15 | $CH_2CH_2COOCH_3$ | Cl | Cl | H | $CH_3$ | 1 |
| 16 | $CH_2CH_2COOCH_3$ | Cl | Cl | H | Et | 1 |
| 17 | $CH_2CH_2C(=O)NH_2$ | Cl | Cl | H | Et | 1 |
| 18 | $CH_2CH_2C(=O)NH_2$ | Cl | Cl | H | $CH_3$ | 1 |
| 19 | $CH_2CH_2COOEt$ | Cl | Cl | H | Et | 0 |
| 20 | $CH_3COOEt$ | Cl | Cl | H | Et | 0 |
| 21 | H | Cl | H | H | $CH_3$ | 1 |
| 22 | H | Cl | H | H | Et | 1 |
| 23 | H | Br | H | H | Et | 1 |
| 24 | —CH=CH(OCH_3) | Cl | Cl | H | Et | 1 |
| 25 | $CH_2CH_2S(=O)CH_3$ | Cl | Cl | H | Et | 1 |
| 26 | $CH_2OCH_3$ | Cl | Cl | H | Et | 1 |

METHODS OR PROCESSES OF SYNTHESIS

The compounds of formula (I) can be prepared according to the manufacturing processes described in International Patent Publications Nos. WO 94/21606 and WO 93/06089 or International Patent Publication No. WO 87/03781 as well as in European Patent Publication No. 0295117 and Hatton et al U.S. Pat. No. 5,232,940. Those skilled in the art will choose the proper initial reactant in these known methods and adapt these known methods to the said reactant so as to obtain the corresponding desired products.

The first method of preparation proceeds according to the following scheme:

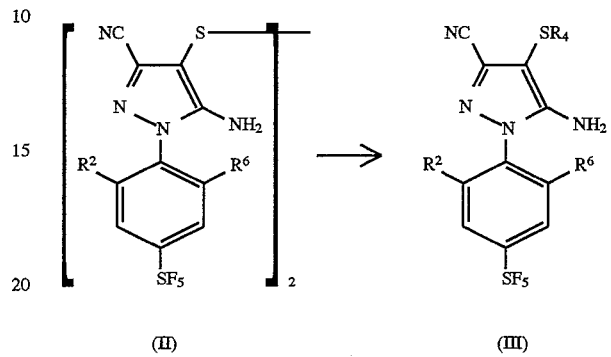

(II)    (III)

wherein $R^2$, $R^4$ and $R^6$ are as defined above.

The reactant of formula (II) above can also be depicted as follows:

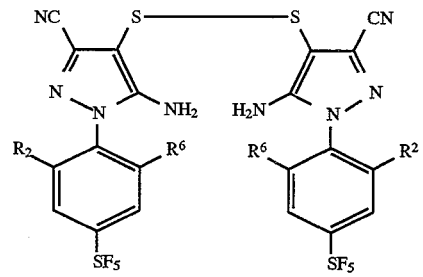

Transformation of (II) to (III) can be achieved by reducing the disulfide (II) with an appropriate reducing agent such as sodium borohydride, to the intermediate sulfide or thiolate, followed by reacting the intermediate with an appropriate alkylating agent, such as an alkyl halide or a dialkyl sulfate, in a suitable solvent such as alcohol, water or ether or a mixture thereof. The reaction can be carded out at a temperature of from about −20° C. to about 150° C., preferably at room temperature.

A second method for the preparation of the compounds of formula (III) is according to the following scheme:

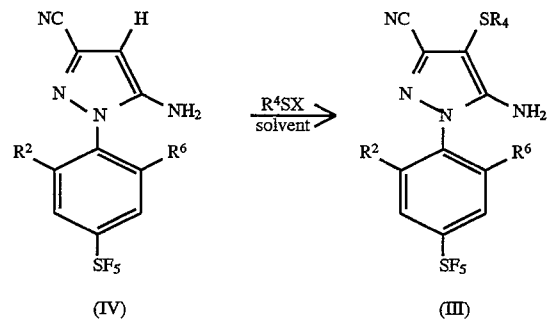

(IV)    (III)

wherein $R^2$, $R^6$ and $R^4$ are as defined with formula (I) and X is halogen.

The transformation of the compounds of formula (IV) to the compounds of formula (III) can be achieved by the direct alkylation of the appropriate alkylsulfenyl halides (also known as alkylthio halides), such as methylsulfenyl chloride or ethylsulfenyl chloride.

The alkylsulfenyl halides can be prepared in a separate pot or they can be generated in situ in the reaction medium for the alkylation of the analogs of the formula (IV). The solvent to be used can be protic or aprotic or a mixture of both.

Examples of aprotic solvents for use in the above process include: amides, such as dimethylformamide (DMF); ethers, such as methyl t-butyl ether, ethyl ether, tetrahydrofuran and dimethoxyethane; haloalkanes, such as methylene chloride; and aromatic solvents such as toluene and chlorobenzene. Examples of protic solvents for use herein are: alcohols, such as methanol and ethanol; amines; and water. The reaction can be conducted in the presence of a catalyst such as a basic catalyst, for example, a metal carbonate, a metal hydride, such as sodium hydride, or a metal hydroxide, such as sodium hydroxide. The reaction can be carried out at a temperature of from about −20° C. to about 150° C., preferably at a temperature of from about 0° C. to about 100° C.

The synthesis of higher oxidation states of the compounds of formula (I), i.e., compounds in which n is 1 or 2, can be achieved by oxidation of the corresponding compounds of formula (III). Alternatively, direct alkylation of the compounds of formula (IV) with an appropriate alkylthio halide $R^4S(O)_nX$ can be carried out according to the scheme:

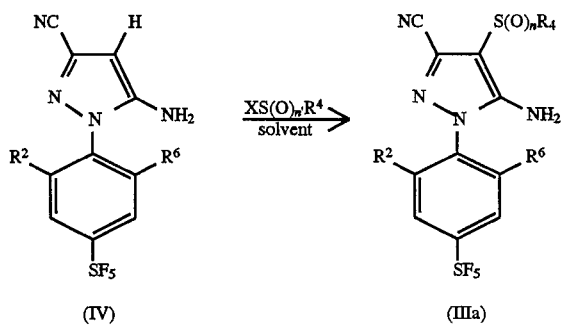

wherein $R^2$, $R^6$ and $R^4$ are as defined with formula (I) above, n' is 1 or 2 and X is halogen (Cl, Br, I or F), to afford the more highly oxidized compounds of formula (IIIa). Illustrative alkylating agents include $CH_3S(O)Cl$, $CH_3CH_2S(O)Cl$ and $(CH_3)_2CHS(O)_2Br$. The reaction conditions and solvents that can be employed to achieve the transformation are similar to those described for alkylations above.

For the synthesis of 5-alkylamino analogs, including the monoalkylamino and dialkylamino derivatives of formula (I) as well as the cyclic amino compounds (i.e., the compounds in which $R^1$ and $R^3$ are joined together) of formula (I), three basic methods are appropriate. The first method includes direct alkylation of precursor compounds of formula (III) or (IIIa) with alkylating agents. The second method involves a two-step sequence, with formation of the imino ethers, followed by a reduction. The third method of preparation is through a conjugate addition, e.g., a Michael-type addition. The compounds of formula (I) in which $R^1$ and/or $R^3$ is/are lower alkyl-$S(O)_n$, formyl, alkenyl, alkynyl, alkoxycarbonyl, alkylthiocarbonyl, aroyl or alkylcarbonyl can be prepared by methods described in one or more of International Publications No. WO 94/21606, WO 93/06089 and WO 87/03781, European Patent Publication No. 0295117 and Hatton et al U.S. Pat. No. 5,232,940.

Synthesis of the precursor compounds of general formulas (II) and (IV) can be achieved according to variations of known methods, for example, those described in GB 8531485 and GB 9201636, as well as in Hatton et al U.S. Pat. No. 5,232,940.

The present invention provides a method for controlling pests at a locus comprising applying to said locus a pesticidally effective amount of a compound of formula (I). The compound of formula (I) can be conveniently used in the form of a composition comprising said compound and an agriculturally acceptable inert carrier therefor. In a preferred embodiment, the pests whose control is desired are arthropods, and an arthropodicidally effective amount of said compounds is applied to the locus. In a more preferred embodiment, the arthropods whose control is desired are insects, and to that end the invention provides a method for controlling insects at a locus comprising applying to said locus an insecticidally effective amount of a compound of formula (I), or an insecticidally effective amount of an insecticidal composition comprising an insecticidally effective amount of a compound of formula (I) and an agriculturally acceptable inert carrier therefor. In another preferred embodiment, control of nematodes is desired, and to that end the invention provides a method of controlling nematodes at a locus comprising applying to said locus a nematocidally effective amount of a compound of formula (I), or a nematocidally effective amount of a nematocidal composition comprising a nematocidally effective amount of a compound of formula (I) and an agriculturally acceptable inert carrier therefor. Preferably, the locus to which the pesticidally, particularly arthropodicidally (especially insecticidally) or nematocidally, effective amount is applied is a crop or a crop-growing area, that is, an area in which a crop is growing or in which a crop has been planted, or an area in which a crop will be planted/grown, particularly where a pesticidal attack is expected or has started.

The compositions which can be used in the invention for the pesticidal, particularly the arthropodicidal (especially insecticidal) or nematocidal, treatment of the invention can comprise from about 0.001 to about 95% of the active ingredient of formula (I). The term "active ingredient of formula (I)" or "active ingredient" as used herein refers to a compound of formula (I) as defined hereinabove unless otherwise specified.

The diluted liquid formulations, as applied to the crop or to the locus where insects are expected to be, generally comprise from about 0.001 to about 3% of active ingredient of formula (I), preferably from about 0.1 to about 0.5%.

The solid formulations as applied to the locus or crop generally comprise from about 0.1 to about 8% of active ingredient of formula (I), preferably from about 0.5 to about 1.5%.

The concentrated compositions are the compositions which are commercialized or transported or stored. For application to plants, they are normally diluted in water and applied in such diluted form. The diluted forms are part of the invention as well as the concentrated forms.

The concentrated formulations generally comprise from about 5 to about 95% of active ingredient of formula (I), preferably from about 10 to about 50%.

The insecticidal compositions of the invention can be applied once, or more than once, or throughout the whole insect season. Insecticidal compositions according to the invention are usually applied to the crop area (or the locus at which a pesticidal attack is expected or started) at a rate of from about 0.04 to about 1 kg/ha of active ingredient, preferably from about 0.1 to about 0.5 kg/ha.

The concentrated insecticidal compositions according to the invention can be in the form of a solid, e.g., dusts or granules or wettable powders, or, preferably, in the form of a liquid, such as an emulsifiable concentrate or a true solution.

The compositions according to the instant invention generally comprise from about 0.5 to about 95% of active ingredient. The remainder of the composition up to 100% comprises a carrier as well as various additives such as those hereafter indicated.

By "carrier", there is meant herein an organic or inorganic material, which may be natural or artificial or synthetic, and which is associated with the active ingredient and which facilitates its application to the crop or other locus to be treated. This carrier is thus generally inert and should be agriculturally acceptable, especially on the contemplated or treated locus or crop. The carrier can be solid (clay, silicates, silica, resins, wax, fertilizers, etc.) or liquid (water, alcohols, ketones, oil solvents, saturated or unsaturated hydrocarbons, chlorinated hydrocarbons, liquefied gas, etc.).

Among the many additives, the compositions of the invention can comprise surfactants as well as other ingredients such as dispersants, stickers, antifoam agents, antifreezing agents, dyestuffs, thickeners, adhesives, protecting colloids, penetrating agents, stabilizing agents, sequestering agents, antiflocculating agents, corrosion inhibitors, pigments and polymers.

More generally, the compositions of the invention can comprise all kind of solid or liquid additives which are known in the art of insecticides and insecticidal treatments.

The surfactants can be of the emulsifying or wetting type, ionic or non-ionic. Possible surfactants are salts of polyacrylic or lignosulfonic acids; salts of phenolsulfonic or naphthalenesulfonic acids; polycondensates of ethylene oxide with fatty alcohols or fatty acids or fatty amines or substituted phenols (particularly alkylphenols or arylphenols); ester-salts of sulfosuccinic acids; taurine derivatives such as alkyl taurates; phosphoric esters; or esters of alcohols or polyoxyethylated phenols. When the spraying vehicle is water, the use of at least one surfactant is generally required because the active ingredients are not water-soluble.

The method of application of the compositions of the invention is generally the spraying of a mixture which has been previously made by dilution of more concentrated formulations according to the invention.

Solid compositions can be powders for dusting or for dispersion (wherein the content of active ingredient can be up to 100%) and granules, especially extruded or compacted granules, or granules which have been made by impregnation of a powder (the content of active ingredients in such powders then being between about 1 and about 80%).

Liquid compositions or compositions which have to be liquid when applied include solutions, water-soluble concentrates, emulsifiable concentrates, emulsions, wettable powders or pastes, or water-dispersible granules.

Emulsifiable concentrates generally comprise from about 10 to about 80% of active ingredient; the emulsions when applied generally comprise from about 0.01 to about 20% of active ingredient.

For example, the emulsifiable concentrates can comprise the solvent and further, to the extent needed, from about 2 to about 20% of suitable additives such as stabilizers, surfactants, penetrating agents, corrosion inhibitors or other additives already recited.

These concentrates are usually diluted in tank water so as to obtain the dilution appropriate for spraying.

The concentrated suspensions can also be applied by spraying and have to be fluid without allowing any solid to separate and fall to the bottom. Generally they comprise from about 1 to about 75% of active ingredient (preferably from about 2 to about 50%), from about 0.5 to about 15% of surfactant, from about 0.1 to about 10% of thickener, and from 0 to about 10% of other suitable additives as already indicated, the remainder being water or an organic liquid in which the active ingredient is insoluble or has a low solubility.

The wettable powders generally comprise the active ingredient (from about 1 to about 95%, preferably from about 2 to about 80%), the solid carrier, a wetting agent (from 0 to about 5%), a dispersing agent (from about 3 to about 10%) and, to the extent needed, from 0 to about 10% of other additives such as stabilizers and other as already listed.

In order to obtain these wettable powders or dusting powders, it is appropriate to intimately mix the active ingredients and the additives, as by grinding in a mill or similar device.

Dispersible granules are generally made by agglomeration of a powder followed by an appropriate granulation process.

The emulsions herein described can be of oil-in-water or water-in-oil types. They can be more or less thick, even approaching the viscosity of a gel.

Among these many compositions or formulations, one skilled in the art can choose the most appropriate one according the specific conditions of the treatment problem that exists.

The compounds and compositions of the invention can also be used in admixtures with another pesticide, e.g., an insecticide, acaricide or herbicide.

The invention is illustrated by the following examples which are not considered as limiting the invention but are given to better enable use of it.

EXAMPLE 1

Preparation of 1-(2,6-dichloro-4-pentafluorothio) phenyl-3-cyano-4-methanesulfenyl-5-aminopyrazole (Compound No. 1)

I) Preparation of methanesulfenyl chloride:

To 3.16 g of dimethyldisulfide was added 40 ml of methyl t-butyl ether, followed by the addition of 1.48 g of sulfuryl chloride. The mixture was stirred at room temperature for 5 hours. A 0.6 ml portion of the resultant solution was used in the following reaction.

II) Methanesulfenylation:

A mixture of 40 mg of 1-(2,6-dichloro-4-pentafluorothio) phenyl-3-cyano-5-aminopyrazole in 5 ml of methyl t-butyl ether was heated to reflux under an inert atmosphere. Methanesulfenyl chloride (0.6 ml solution in methyl-t-butyl ether) was added and the mixture was heated at reflux for 4 hours. The mixture was cooled to room temperature, then was partitioned between saturated aqueous sodium bicarbonate solution and methylene chloride. The organic layer was washed with water. The organic layer was dried over anhydrous sodium sulfate and the solvent was evaporated. The residue was purified by preparative TLC (thin layer chromatography) using 40% ethyl acetate in hexane to give 1-(2,6-dichloro-4-pentafluorothio)phenyl-3-cyano-4-methanesulfenyl-5-aminopyrazole. H-1 NMR(CDCl$_3$): d 7.8 ppm (2H, s), 2.3 ppm (3H, s).

By proceeding in a similar manner 1-(2,6-dichloro-4-pentafluorothio)phenyl-3-cyano-4-ethanesulfenyl-5-aminopyrazole (Compound No. 3) was prepared, m.p. 164°–167° C.

EXAMPLE 2

Preparation of 1-(2,6-dichloro-4-pentafluorothio)phenyl-3-cyano-4-methanesulfinyl-5-aminopyrazole (Compound No. 2)

To a solution of 20 mg of 1-(2,6-dichloro-4-pentafluorothio)phenyl-3-cyano-4-methanesulfenyl-5-aminopyrazole in 5 ml of methanol was added 0.02 ml of sulfuric acid/isopropanol catalyst solution, followed by the addition of 0.02 ml of 30% hydrogen peroxide at 4° C. The mixture stirred for 2 days while being allowed to warm to room temperature. More (0.02 ml) of $H_2SO_4$/isopropanol solution and 0.02 ml of 30% hydrogen peroxide were added and the mixture was stirred at room temperature overnight. The mixture was partitioned between methylene chloride and water. The organic layer was washed with saturated aqueous sodium bisulfite solution, followed by a wash with saturated aqueous sodium bicarbonate solution and then a wash with water. The organic layer was dried over anhydrous sodium sulfate and the solvent was evaporated. The residue was purified by preparative TLC using 70% ethyl acetate in hexane to give the desired 1-(2,6-dichloro-4-pentafluorothio)phenyl-3-cyano-4-methanesulfinyl-5-aminopyrazole. H-1 NMR(CDCl$_3$): d 7.8 ppm (2H, d), 3.0 ppm (3H, s). By proceeding in a similar manner the following compounds were also prepared:

1-(2,6-dichloro-4-pentafluorothio)phenyl-3-cyano-4-ethanesulfinyl-5-aminopyrazole (Compound No. 4), m.p. 186°–187° C.

1-(2,6-dichloro-4-pentafluorothio)phenyl-3-cyano-4-methanesulfonyl-5-aminopyrazole (Compound No. 6), m.p. 263°–264° C.

The following test methods were used applying representative compounds of the invention hereinabove prepared. The following species were used:

| GENUS, SPECIES | COMMON NAME | ABBREVIATION |
|---|---|---|
| *Aphis gossypii* | cotton leaf aphid | APHIGO |
| *Schizaphis graminum* | greenbug | TOXOGR |
| *Musca domestica* | housefly | MUSCDO |
| *Spodoptera eridania* | southern armyworm | PRODER |
| *Meloidogyne incognita* | southern root-knot nematode | MELGIN |

The Soil Drench Test

In this test representative compounds of the invention were compared with known prior art compounds, 1-(2,6-dichloro-4-pentafluorothio)phenyl-3-cyano-4-trifluoromethanesulfinyl-5-aminopyrazole and the corresponding 4-SO$_2$CF$_3$ compound (Compounds 2 and 3 of WO93/06089), which are hereafter referred to as Compound No. P1 and P2. Cotton and sorghum plants were established in pots. One day prior to treatment, each pot was infested with about 25 aphids of a mixed population. Cotton plants were infested with cotton leaf aphid and sorghum plants were infested with greenbug. Test compound was applied to the soil surface as solutions that delivered the equivalent of 20, 5 and 1.25 ppm soil concentration by weight. Aphid counts were obtained at 5 DAT (days after treatment). The number of aphids on the treated plants was compared to the number of those on the untreated control plants. An LC50 value was calculated for each compound. The following results were obtained:

| | LC$_{50}$ RESULTS (ppm) SPECIES | |
|---|---|---|
| Compound No. | APHIGO | TOXOGR |
| 2 | <10.0 | <10.0 |
| 3 | >10.0 | 6.0 |
| 4 | 3.57 | 0.55 |
| 6 | 1.39 | 1.55 |
| P1 | >20.0 | 4.83 |
| P2 | >10.0 | >10.0 |

Nematode Soil Drench Test

Soil is treated with the test compound to obtain a soil concentration of 10.0 ppm. Juveniles collected and separated from infected tomato roots are introduced to the treated soil. The treated and nematode-infested soil are either planted with tomato seedlings or cotton seeds (both susceptible to nematode attack). After the appropriate interval for plant growth and root-knot formation, the plants are removed from the soil and the roots examined for root-knot formation. Untreated, uninoculated plants has roots free of knots as do plants where the test compounds elicit high activity.

The Housefly Bait/Contact Test

About 25 four to six day old adult houseflies were anesthetized and placed in a cage with a sugar water bait solution containing the test compound. The compound concentration in the bait solution was 100 ppm. After 24 hours, flies which showed no movement on stimulation were considered dead.

A 100% mortality was obtained with representative compounds of the invention.

Foliar/Contact Test with APHIGO

Aphid-infested cotton plants and snapbean plants were placed on a revolving turntable and sprayed to runoff with a 100 ppm formulation of the test compound. The counts of live and dead larvae were made at 5 DAT. The treated APHIGO infested plants were held for three days after treatment, after which the dead aphids were counted.

A 100% mortality was obtained with representative compounds of the invention.

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A compound of the formula:

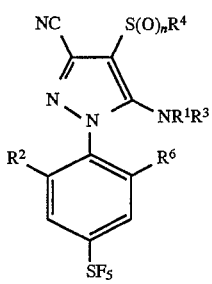

wherein:
  each of $R^2$ and $R^6$, which are identical or different, is hydrogen, halogen, CN, alkyl, haloalkyl or alkylthio;
  n is 0, 1 or 2;
  $R^4$ is lower alkyl;
  each of $R^1$ and $R^3$, which are identical or different, is H, lower alkyl, lower alkyl-$S(O)_n$, formyl, alkenyl, alkynyl, alkoxycarbonyl, alkylthiocarbonyl, aroyl or alkylcarbonyl, the alkyl portion of which radicals is unsubstituted or substituted by one or more $R^5$;
  or $R^1$ and $R^3$ are joined so as together to form a divalent radical having 4 to 6 atoms in the chain, said divalent radical being alkylene, alkyleneoxyalkylene or alkyleneaminoalkylene;
  $R^5$ is cyano, nitro, alkoxy, haloalkoxy, $R^7S(O)_n$, alkoxycarbonyl, alkylcarbonyl, aminocarbonyl, alkylaminocarbonyl, dialkylaminocarbonyl, hydroxycarbonyl, halogen, hydroxy, aminosulfonyl, alkylaminosulfonyl or dialkylaminosulfonyl; and
  $R^7$ is lower alkyl or lower haloalkyl.

2. The compound according to claim 1, wherein each of $R^2$ and $R^6$, which are identical or different, is H, Cl, Br or F.

3. The compound according to claim 1 wherein $R^4$ is methyl, ethyl or propyl.

4. The compound according to claim 2 wherein $R^4$ is methyl, ethyl or propyl.

5. The compound according to claim 2 wherein $R^2$ and $R^6$ are chlorine.

6. The compound according to claim 3 wherein $R^2$ and $R^6$ are chlorine.

7. The compound according to claim 1 wherein $R^1$ is hydrogen and $R^3$ is hydrogen or lower alkyl.

8. The compound according to claim 3 wherein $R^1$ is hydrogen and $R^3$ is hydrogen or lower alkyl.

9. The compound according to claim 5 wherein $R^1$ is hydrogen and $R^3$ is hydrogen or lower alkyl.

10. The compound according to claim 1 wherein $R^1$ and $R^3$ are hydrogen.

11. The compound according to claim 7 wherein $R^1$ and $R^3$ are hydrogen.

12. The compound according to claim 1, wherein:
  $R^1$ and $R^3$ each represent hydrogen;
  $R^2$ and $R^6$ each represent chlorine;
  $R^4$ represents methyl or ethyl;
  and n is zero, 1 or 2.

13. The compound according to claim 1, which is:
  (a) 1-(2,6-dichloro-4-pentafluorothio)phenyl-3-cyano-4-methanesulfenyl-5-aminopyrazole;
  (b) 1-(2,6-dichloro-4-pentafluorothio)phenyl-3-cyano-4-methanesulfinyl-5-aminopyrazole;
  (c) 1-(2,6-dichloro-4-pentafluorothio)phenyl-3-cyano-4-ethanesulfenyl-5-aminopyrazole;
  (d) 1-(2,6-dichloro-4-pentafluorothio)phenyl-3-cyano-4-ethanesulfinyl-5 aminopyrazole; or
  (e) 1-(2,6-dichloro-4-pentafluorothio)phenyl-3-cyano-4-methanesulfonyl-5-aminopyrazole.

14. A pesticidal composition comprising a pesticidally effective amount of a compound of formula (I)

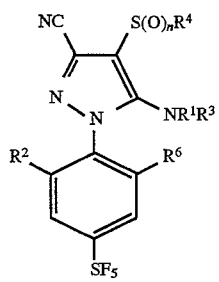

wherein:
  each of $R^2$ and $R^6$, which are identical or different, is hydrogen, halogen, CN, alkyl, haloalkyl or alkylthio;
  n is 0, 1 or 2;
  $R^4$ is lower alkyl;
  each of $R^1$ and $R^3$, which are identical or different, is H, lower alkyl, lower alkyl-$S(O)_n$, formyl, alkenyl, alkynyl, alkoxycarbonyl, alkylthiocarbonyl, aroyl or alkylcarbonyl, the alkyl portion of which radicals is unsubstituted or substituted by one or more $R^5$;
  or $R^1$ and $R^3$ are joined so as together to form a divalent radical having 4 to 6 atoms in the chain, said divalent radical being alkylene, alkyleneoxyalkylene or alkyleneaminoalkylene;
  $R^5$ is cyano, nitro, alkoxy, haloalkoxy, $R^7S(O)_n$, alkoxycarbonyl, alkylcarbonyl, aminocarbonyl, alkylaminocarbonyl, dialkylaminocarbonyl, hydroxycarbonyl, halogen, hydroxy, aminosulfonyl, alkylaminosulfonyl or dialkylaminosulfonyl;
  $R^7$ is lower alkyl or lower haloalkyl; and
  an agriculturally acceptable inert carrier therefor.

15. A pesticidal composition according to claim 14 wherein each of $R^2$ and $R^6$, which are identical or different, is H, Cl, Br or F.

16. A pesticidal composition according to claim 14 wherein $R^4$ is methyl, ethyl or propyl.

17. A method for controlling pests at a locus comprising applying to said locus a pesticidally effective amount of a compound of formula (I)

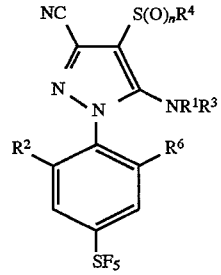

wherein:
  each of $R^2$ and $R^6$, which are identical or different, is hydrogen, halogen, CN, alkyl, haloalkyl or alkylthio;
  n is 0, 1 or 2;
  $R^4$ is lower alkyl;

each of $R^1$ and $R^3$, which are identical or different, is H, lower alkyl, lower alkyl-$S(O)_n$, formyl, alkenyl, alkynyl, alkoxycarbonyl, alkylthiocarbonyl, aroyl or alkylcarbonyl, the alkyl portion of which radicals is unsubstituted or substituted by one or more $R^5$;

or $R^1$ and $R^3$ are joined so as together to form a divalent radical having 4 to 6 atoms in the chain, said divalent radical being alkylene, alkyleneoxyalkylene or alkyleneaminoalkylene;

$R^5$ is cyano, nitro, alkoxy, haloalkoxy, $R^7S(O)_n$, alkoxycarbonyl, alkylcarbonyl, aminocarbonyl, alkylaminocarbonyl, dialkylaminocarbonyl, hydroxycarbonyl, halogen, hydroxy, aminosulfonyl, alkylaminosulfonyl or dialkylaminosulfonyl;

$R^7$ is lower alkyl or lower haloalkyl.

18. A method according to claim 17 wherein each of $R^2$ and $R^6$, which are identical or different, is H, Cl, Br or F.

19. A method according to claim 17 wherein $R^4$ is methyl, ethyl or propyl.

20. The method according to claim 17, wherein said compound is applied to said locus at a rate of from about 0.04 to about 1 kg/ha.

21. A process for the preparation of a compound according to claim 1, said process comprising:

(a) where n is zero and $R^1$ and $R^3$ are hydrogen, reacting a compound of formula (II):

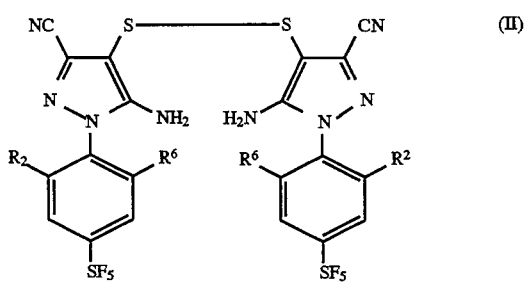

wherein $R^2$ and $R^6$ are as defined in claim 1, with a reducing agent, followed by reacting the intermediate sulfide or thiolate thus obtained with an alkylating agent;

(b) where $R^1$ and $R^3$ are hydrogen, reacting a compound of formula (IV):

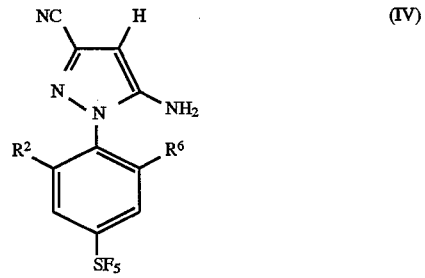

wherein $R^2$ and $R^6$ are as defined in claim 1, with a compound of formula $R^4S(O)_nX$, wherein $R^4$ and n are as defined in claim 1 and X is halogen;

(c) where n is one or two, oxidizing the corresponding compound of formula (I) in which n is zero or one; or (d) where one or both of $R^1$ and $R^3$ are alkyl, or $R^1$ and $R^3$ are joined so as together to form a divalent radical having 4 to 6 atoms in the chain, this divalent radical being alkylene, alkyleneoxyalkylene or alkyleneaminoalkylene, the reaction of the corresponding compound of formula (I) in which $R^1$ or $R^3$ are hydrogen with an alkylating agent.

* * * * *